US006837867B2

(12) United States Patent
Kortelling

(10) Patent No.: US 6,837,867 B2
(45) Date of Patent: Jan. 4, 2005

(54) STEERABLE CATHETER WITH REINFORCED TIP

(75) Inventor: Bart-Jan Kortelling, Mission Viejo, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 251 days.

(21) Appl. No.: 09/846,738

(22) Filed: Apr. 30, 2001

(65) Prior Publication Data

US 2002/0161353 A1 Oct. 31, 2002

(51) Int. Cl.$^7$ ............................................. A61M 31/60
(52) U.S. Cl. ................................ 604/95.04; 604/95.01; 604/585; 606/41
(58) Field of Search ......................... 604/93.01, 95.01, 604/95.54, 585, 527, 281; 606/1, 41, 75

(56) References Cited

U.S. PATENT DOCUMENTS

| | | | |
|---|---|---|---|
| 2,498,692 A | | 2/1950 | Mains ........................ 128/348 |
| 4,686,963 A | * | 8/1987 | Cohen et al. ................ 600/141 |
| 5,195,968 A | | 3/1993 | Lundquist et al. ............ 604/95 |
| 5,199,950 A | | 4/1993 | Schmitt et al. ............... 604/95 |
| 5,254,088 A | | 10/1993 | Lundquist et al. ............ 604/95 |
| 5,318,525 A | | 6/1994 | West et al. .................... 604/95 |
| 5,395,327 A | | 3/1995 | Lundquist et al. ............ 604/95 |
| 5,395,328 A | * | 3/1995 | Ockuly et al. ............... 604/528 |
| 5,456,674 A | | 10/1995 | Bos et al. .................... 604/280 |
| 5,500,012 A | | 3/1996 | Brucker et al. ............. 607/122 |
| 5,507,725 A | | 4/1996 | Savage et al. ................ 604/95 |
| 5,545,200 A | | 8/1996 | West et al. ................. 607/122 |
| 5,674,197 A | | 10/1997 | van Muiden et al. ......... 604/95 |
| 5,676,653 A | | 10/1997 | Taylor et al. ................. 604/95 |
| 5,715,817 A | * | 2/1998 | Stevens-Wright et al. .. 600/373 |
| 5,820,591 A | | 10/1998 | Thompson et al. ........... 604/95 |
| 5,824,031 A | | 10/1998 | Cookston et al. ........... 607/122 |
| 5,906,590 A | | 5/1999 | Hunjan et al. ................ 604/95 |

FOREIGN PATENT DOCUMENTS

EP      0 689 851      1/1996

* cited by examiner

*Primary Examiner*—Thor Campbell
(74) *Attorney, Agent, or Firm*—Christie, Parker & Hale, LLP

(57) ABSTRACT

A steerable catheter having a reinforced distal end for improved deflection is provided. The catheter comprises an elongated, flexible tubular catheter body having proximal and distal ends and a lumen extending therethrough. A tip section is provided at the distal end of the catheter body. The tip section comprises a flexible plastic tubing having at least one off-axis lumen extending therethrough. A control handle is provided at the proximal end of the catheter body. At least one puller wire extends through the off-axis lumen of the tip section and lumen of the catheter body. The puller wire has a proximal end anchored to the control handle and a distal end anchored to the tip section. The puller wire is longitudinally moveable relative to the catheter body to cause deflection of the tip section in a plane in a first direction. The catheter further comprises one or more stabilizing features extending longitudinally along at least a portion of the length of the tip section and positioned generally symmetrically about a diameter of the tip section corresponding to the plane in which the tip section is deflectable. The one or more stabilizing features comprise a material that has a higher modulus of elasticity than the plastic of the tip section.

35 Claims, 5 Drawing Sheets

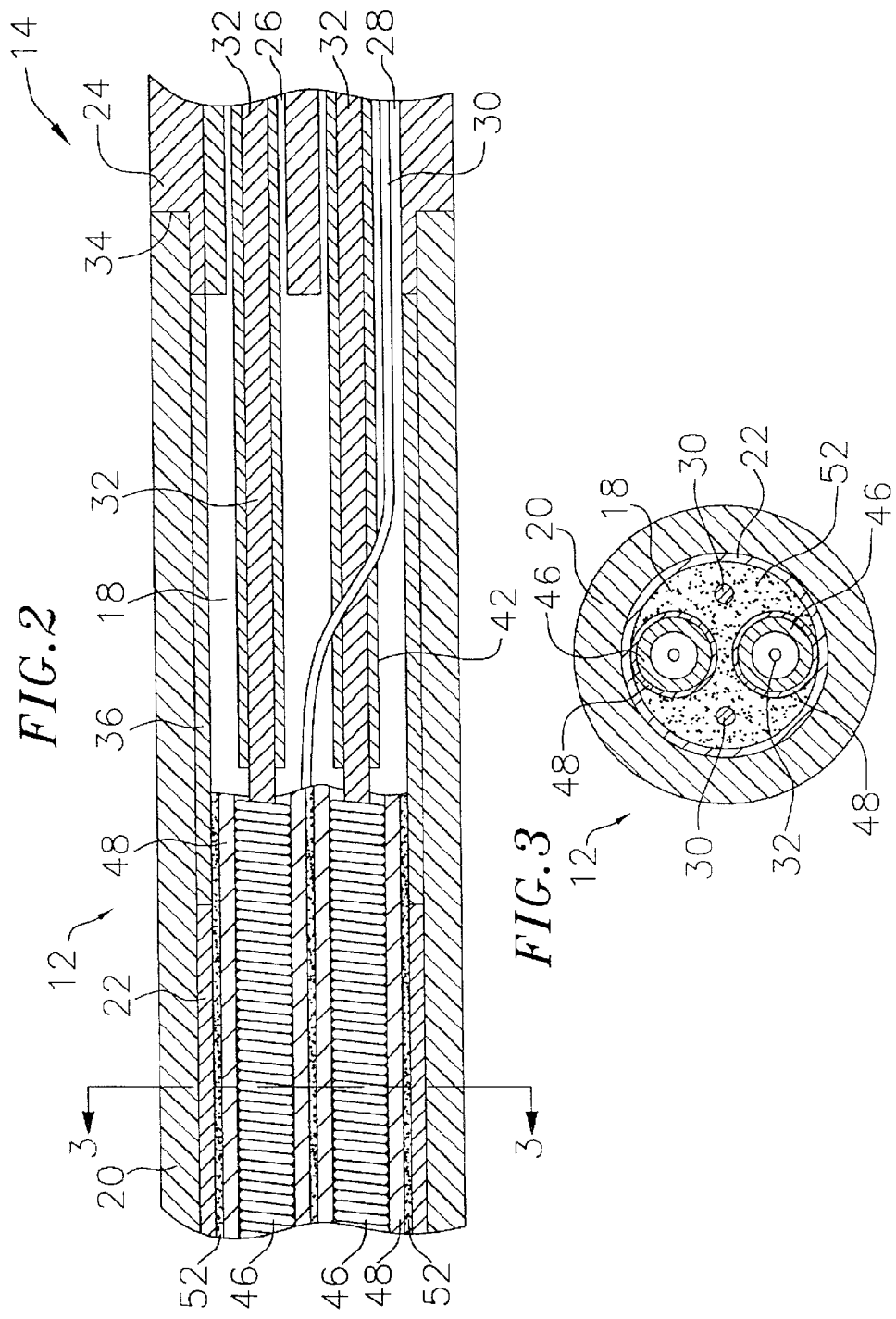

US 6,837,867 B2

STEERABLE CATHETER WITH REINFORCED TIP

FIELD OF THE INVENTION

The present invention relates to an improved steerable catheter having a reinforced distal end to improve deflection.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Steerable (or deflectable) catheters are generally well-known. For example, U.S. Pat. No. RE 34,502 describes a catheter having a control handle comprising a housing having a piston chamber at its distal end. A piston is mounted in the piston chamber and is afforded lengthwise movement. The proximal end of the catheter body is attached to the piston. A puller wire is attached to the housing and extends through the piston and through the catheter body. The distal end of the puller wire is anchored in the tip section of the catheter. In this arrangement, lengthwise movement of the piston relative to the housing results in deflection of the catheter tip section.

Often it is desirable to have a bidirectional steerable catheter, i.e., a catheter that can be deflected in two directions, typically opposing directions. For example, U.S. Pat. No. 6,210,407 discloses a bidirectional steerable catheter having two puller wires extending through the catheter. The distal ends of the puller wires are anchored to opposite sides of the tip section of the catheter. A suitable bidirectional control handle is provided that permits longitudinal movement of each puller wire to thereby allow deflection of the catheter in two opposing directions.

Regardless of whether the catheter is unidirectional or bidirectional, it is typically preferred that the tip section can be deflected in the plane of the catheter so that the catheter can be more precisely controlled in the heart. However, because the tip section is generally made of a flexible material, it is sometimes difficult to limit out-of-plane deflection. Accordingly, a need exists for a catheter having a tip section that can be consistently deflected within the plane of the catheter.

SUMMARY OF THE INVENTION

A steerable catheter having a reinforced distal end for improved deflection is provided. The catheter comprises an elongated, flexible tubular catheter body having proximal and distal ends and a lumen extending therethrough. A tip section is provided at the distal end of the catheter body. The tip section comprises a flexible plastic tubing having at least one off-axis lumen extending therethrough. A control handle is provided at the proximal end of the catheter body. At least one puller wire extends through the off-axis lumen of the tip section and lumen of the catheter body. The puller wire has a proximal end anchored to the control handle and a distal end anchored to the tip section. The puller wire is longitudinally moveable relative to the catheter body to cause deflection of the tip section in a plane in a first direction. The catheter further comprises one or more stabilizing features extending longitudinally along at least a portion of the length of the tip section and positioned generally symmetrically about a diameter of the tip section corresponding to the plane in which the tip section is deflectable. The one or more stabilizing features comprise a material that has a higher modulus of elasticity than the plastic of the tip section. The inventive catheter can be a bidirectional catheter, having two puller wires extending through opposing off-axis lumens.

DESCRIPTION OF THE DRAWINGS

These and other features of the advantages of the present invention will be better understood by reference to the following detailed description when considered in conjunction with the accompanying drawings wherein:

FIG. 2 is a side cross-sectional view of the junction of the catheter body and tip section of an embodiment of a catheter according to the invention.

FIG. 3 is a transverse cross-sectional view of the catheter body shown in FIG. 2 taken along line 3—3.

DETAILED DESCRIPTION

Figure 1:
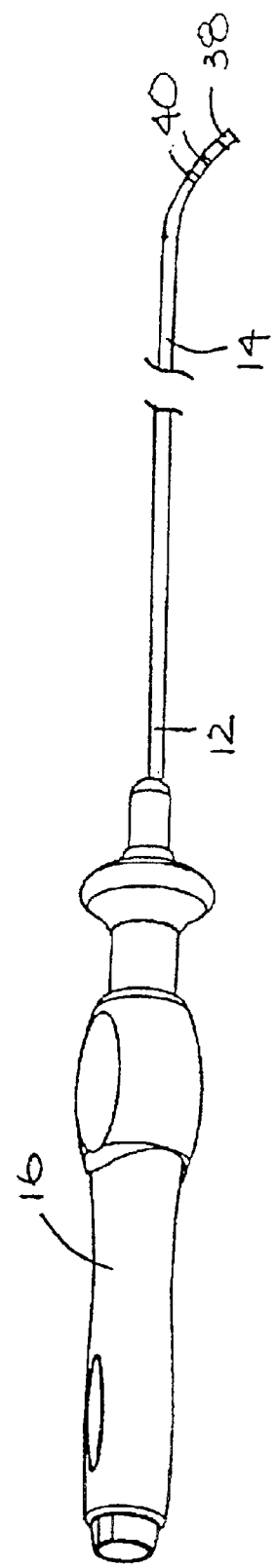
FIG. 1 is a side view of an embodiment of the catheter of the invention.

In a particularly preferred embodiment of the invention, there is provided a steerable bidirectional electrode catheter. As shown in FIG. 1, the catheter 10 comprises an elongated catheter body 12 having proximal and distal ends, a tip section 14 at the distal end of the catheter body 12, and a control handle 16 at the proximal end of the catheter body 12.

As shown in FIGS. 2 and 3, the catheter body 12 comprises an elongated tubular construction having a single axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 preferably comprises an imbedded braided mesh of stainless steel or the like to increase torsional stiffness of the catheter body 12 so that when the control handle 16 is rotated the tip section 14 will rotate in a corresponding manner.

The overall length and diameter of the catheter 10 may vary according to the application. A presently preferred catheter 10 has an overall length of about 48 inches. The outer diameter of the catheter body 12 is not critical, but is preferably no more than about 8 french. The inner surface of the outer wall 20 is preferably lined with a stiffening tube 22, which can be made of any suitable material, preferably nylon or polyimide. The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. A particularly preferred catheter 10 has an outer diameter of about 0.092 inch and a lumen 18 diameter of about 0.052 inch. If desired, the stiffening tube can be omitted.

Figure 5:
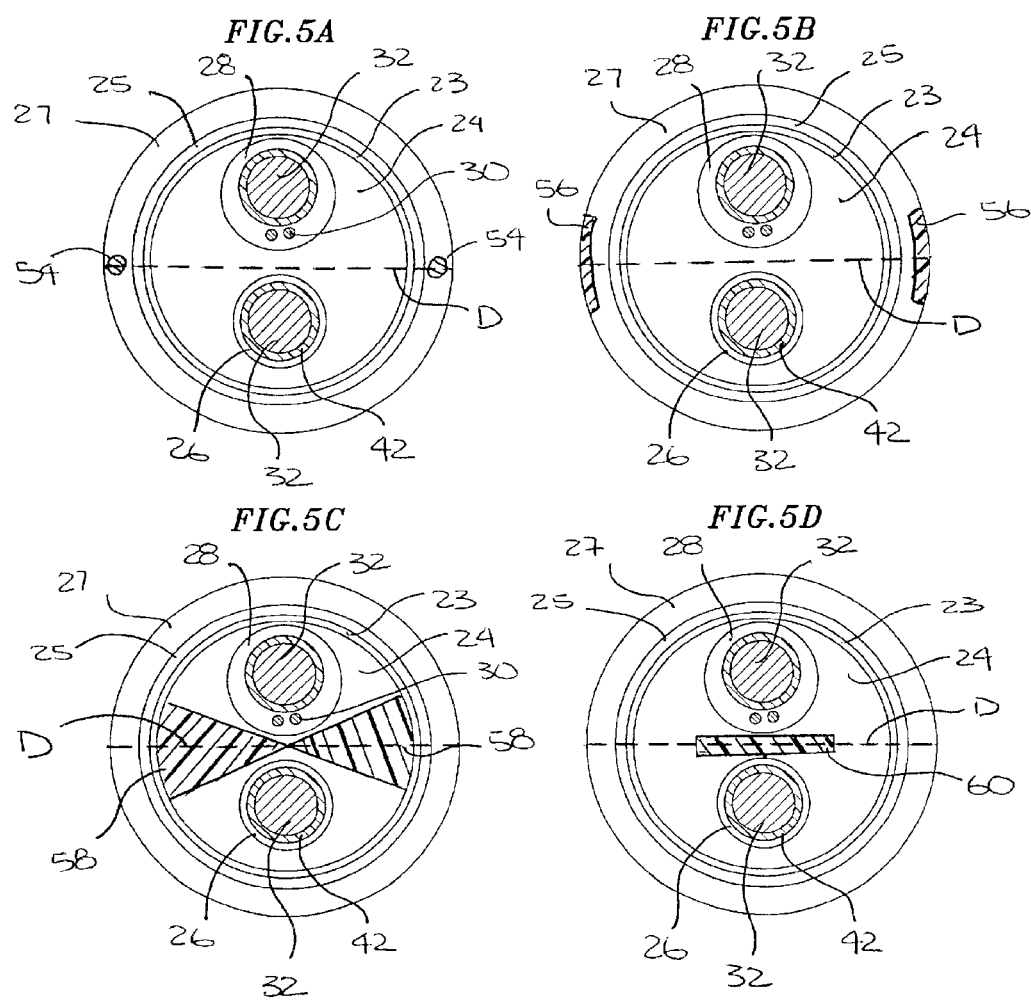
FIG. 5A is a transverse cross-sectional view of the tip section along line 5—5 where the tip section has two rods in the outer layer as stabilizing features.
FIG. 5B is a transverse cross-sectional view of an alternative embodiment of a tip section having two strips in the outer layer as stabilizing features.
FIG. 5C is a transverse cross-sectional view of an alternative embodiment of a tip section having two pie-shaped stabilizing features in the core.
FIG. 5D is a transverse cross-sectional view of an alternative embodiment of a tip section having a single bar-shaped stabilizing features in the core.

As shown in FIG. 5A, the tip section 14 comprises a short section of flexible tubing comprising a core 24, an inner layer 23 surrounding the core, a braided mesh 25 surrounding the inner layer, and an outer layer 27 surrounding the braid. The core 24 is formed of a suitable non-toxic plastic, preferably polyurethane or PEBAX, and has a first off-axis lumen 26 and a second off-axis lumen 28 extending therethrough. The core 24 is preferably made by extruding the plastic over two mandrels to thereby form the two off-axis lumens 26 and 28, where the mandrels are removed after the core is extruded. The inner layer 23, which is also made of plastic, preferably polyurethane or PEBAX, is formed over the core 24 by any suitable technique, such as extrusion, which can be performed simultaneously with the extrusion of the core.

Thereafter, the braided mesh 25 is formed over the inner layer 23. The braided mesh 25 comprises interwoven helical members, typically twelve, sixteen or twenty-four interwoven helical members, half extending in one direction and the other half extending in the in the counter direction. The tightness or braid angle of the helical members to a line parallel with the axis of the catheter and intersecting the helical members is not critical, but is preferably about 45°. The helical members are preferably made of a conductive material having a high modulus of elasticity. Preferred helical members are made of stainless steel wire. Other methods for forming a braided mesh known in the art may be used.

Finally the outer layer 27, which is also made of a suitable plastic such as polyurethane or PEBAX, is formed over the braided mesh 25 by any suitable technique, preferably extrusion. As would be recognized by one skilled in the art, the specific number and composition of the layers of the tip section 14 is not critical. For example, the inner layer 24 can be omitted, particularly if it is desired to have a relatively small diameter tip section. The braided mesh 25 can also be omitted, in which case the tip section 14 can optionally comprise a unitary core 24 formed without additional plastic layers. Preferably whatever design is used, the tip section 14 is more flexible than the catheter body 12. The outer diameter of the tip section 14, like that of the catheter body 12, is preferably no greater than about 8 french, more preferably about 6½ french or less, but can vary depending on the particular application for which the catheter is to be used.

The off-axis lumens 26 and 28 extend through diametrically opposed halves of the tip section 14. In the depicted embodiment, the off-axis lumens 26 and 28 are asymmetrical and therefore non-interchangeable. The first off-axis lumen 26 is smaller than the second off-axis lumen 28. In an 8 French or 7 French diameter catheter, where the tip section is 6½ French, it is preferred that the first off-axis lumen 26 has a diameter ranging from about 0.018 inch to about 0.025 inch, more preferably from about 0.018 inch to about 0.022 inch. Preferably, the second off-axis lumen 28 has a diameter ranging from about 0.022 inch to about 0.030 inch, more preferably from about 0.026 inch to about 0.028 inch. By using two rather than three lumens along a single diameter, the present design retains the simplified construction of the unidirectional deflectable steerable catheter described in U.S. Pat. No. Re 34,502, which is incorporated herein by reference. However, the number and size of the lumens in the tip section is not critical to the present invention and can vary as desired.

A preferred means for attaching the catheter body 12 to the tip section 14 is illustrated in FIG. 2. The proximal end of the tip section 14 comprises an outer circumferential notch 34 that receives the inner surface of the outer wall 20 of the catheter body 12. The tip section 14 and catheter body 12 are attached by glue or the like. Before the tip section 14 and catheter body 12 are attached, however, the stiffening tube 22 is inserted into the catheter body 12. The distal end of the stiffening tube 22 is fixedly attached near the distal end of the catheter body 12 by forming a glue joint with polyurethane glue or the like. Preferably a small distance, e.g., about 3 mm, is provided between the distal end of the catheter body 12 and the distal end of the stiffening tube 22 to permit room for the catheter body 12 to receive the notch 34 of the tip section 14. A force is applied to the proximal end of the stiffening tube 22, and, while the stiffening tube 22 is under compression, a first glue joint (not shown) is made between the stiffening tube 22 and the outer wall 20 by a fast drying glue, e.g. Super Glue®. Thereafter a second glue joint is formed between the proximal ends of the stiffening tube 22 and outer wall 20 using a slower drying but stronger glue, e.g., polyurethane. Other suitable techniques for attaching the catheter body 12 and tip section 14 can also be used in accordance with the present invention.

In the depicted embodiment, a spacer 36 lies within the catheter body 12 between the distal end of the stiffening tube 22 and the proximal end of the tip section 14. The spacer 36 is preferably made of a material that is stiffer than the material of the tip section 14, e.g., polyurethane, but not as stiff as the material of the stiffening tube 22, e.g. polyimide. A spacer made of Teflon® is presently preferred. A preferred spacer 36 has a length of from about 0.25 inch to about 0.75 inch, more preferably about 0.50 inch. Preferably the spacer 36 has an outer and inner diameter about the same as the outer and inner diameters of the stiffening tube 22. The spacer 36 provides a transition in flexibility at the junction of the catheter body 12 and the tip section 14 to bend smoothly without folding or kinking. If desired, the spacer 36 can be omitted.

Figure 4:
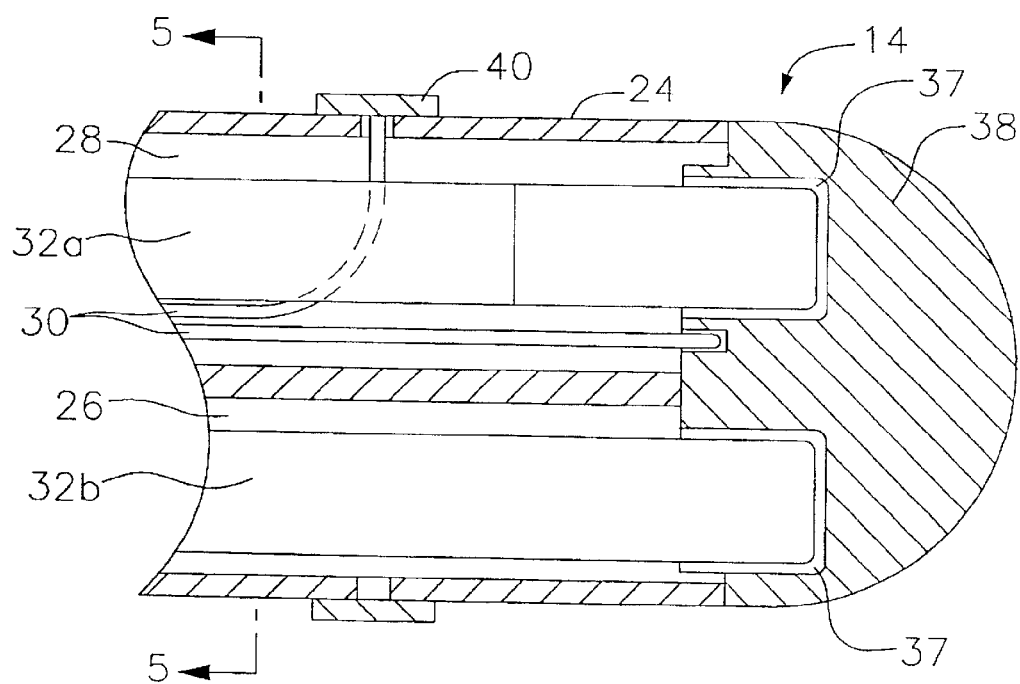
FIG. 4 is a side cross-sectional view of the distal end of the tip section shown in FIG. 2.

FIG. 4 provides a schematic side cross-sectional view of the tip section 14, but does not depict the various layers described above for simplicity. As shown in FIG. 4, the distal end of the tip section 14 carries a tip electrode 38. Mounted along the length of the tip section 14 is a ring electrode 40. The length of the ring electrode 40 is not critical, but preferably ranges from about 1 mm to about 3 mm. Additional ring electrodes can be provided if desired. If multiple ring electrodes are used, they are spaced apart in any fashion as desired so long as their edges do not touch.

The tip electrode 38 and ring electrode 40 are each connected to a separate lead wire 30. Each lead wire 30 extends through the second off-axis lumen 28 in the tip section 14, through the central lumen 18 in the catheter body 12 and through the control handle 16. The proximal end of each lead wire 30 extends out the proximal end of the control handle 16 and is connected to an appropriate connector, which can be plugged into or otherwise connected to a suitable monitor, source of energy, etc.

The lead wires 30 are connected to the tip electrode 38 and ring electrode 40 by any conventional technique. Connection of a lead wire 30 to the tip electrode 38 is preferably accomplished by solder or the like. Connection of a lead wire 30 to a ring electrode 40 is preferably accomplished by first making a small hole through the wall of the tip section 14 into the second lumen 28 through which the lead wire extends. Such a hole can be created, for example, by inserting a needle through the wall of the tip section 14 and heating the needle sufficiently to form a permanent hole. A lead wire 30 is then drawn through the hole by using a microhook or the like. The end of the lead wire 30 is then stripped of any coating and welded to the underside of the ring electrode 40, which is then slid into position over the hole and fixed in place with polyurethane glue or the like.

Two puller wires 32 extend through the catheter 10. Each puller wire 32 extends from the control handle 16, through the central lumen 18 in the catheter body 12 and into one of the off-axis lumens 26 and 28 of the tip section 14. As described in more detail below, the proximal end of each puller wire 32 is anchored within the control handle 16 and the distal end of each puller wire 32 is anchored within the tip section 14.

Each puller wire 32 is made of any suitable metal, such as stainless steel or Nitinol. Preferably each puller wire 32 has a coating, such as a coating of Teflon® or the like. Each puller wire 32 has a diameter preferably ranging from about 0.006 inch to about 0.0010 inch. Preferably both of the puller wires 32 have the same diameter.

Each puller wire 32 is anchored near the distal end of the tip section 14. In the embodiment depicted in FIG. 4, the puller wires 32 are both anchored in blind holes 37 in the tip electrode 38 by a welding or the like.

Figure 6:
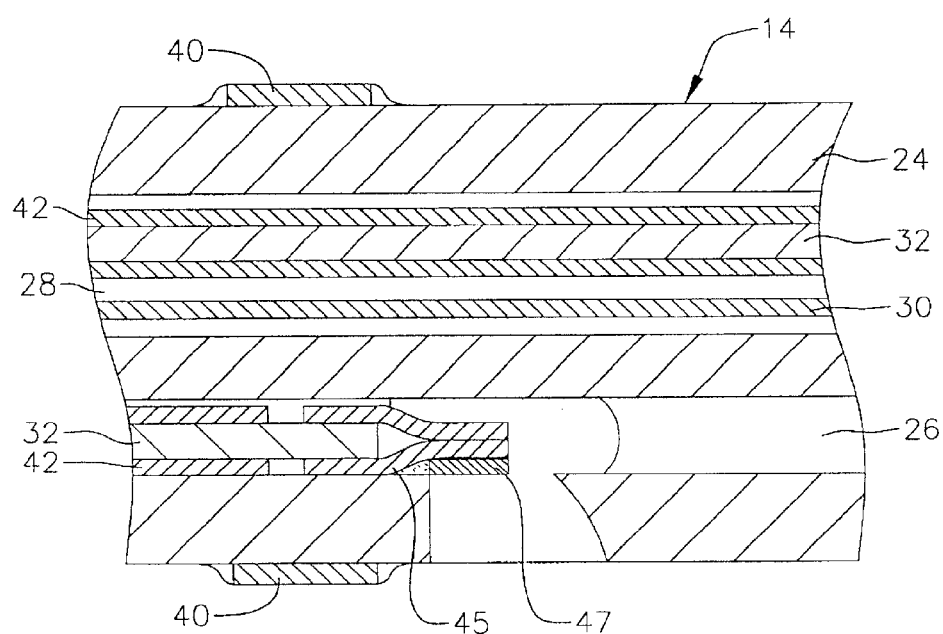
FIG. 6 is a transverse cross-sectional view of a catheter tip section according to the invention where the puller wires are anchored to the side walls of the tip section.
Figure 7:
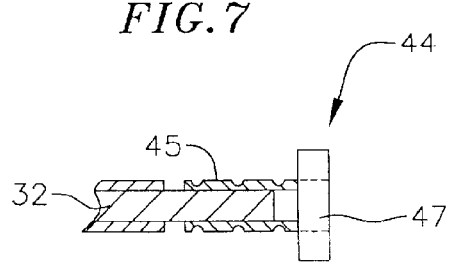
FIG. 7 is a longitudinal cross-sectional view of a preferred puller wire T-bar anchor.
Figure 8:
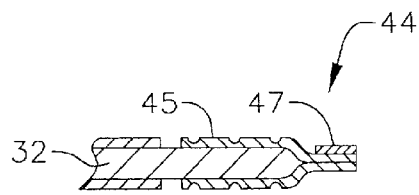
FIG. 8 is a longitudinal cross-sectional view of the puller wire T-bar anchor of FIG. 7 rotated 90° to show the cross-piece on end.

Alternatively, one or both puller wires 32 can be anchored to the side wall of the tip section 14. In the alternative embodiment of FIGS. 6 to 8, the puller wire 32 in the first off-axis lumen 26 is anchored to the side wall of the tip section 14 and attached by means of an anchor 44 fixedly attached to the distal end of the puller wire 32. The anchor 44 is formed by a metal tube 45, e.g., a short segment of hypodermic stock, that is fixedly attached, e.g. by crimping, to the distal end of the puller wire 32. The tube has a section that extends a short distance beyond the distal end of the puller wire 32. A cross-piece 47 made of a small section of stainless steel ribbon or the like is soldered or welded in a transverse arrangement to the distal end of the metal tube which is flattened during the operation. This creates a T-bar anchor 44. A notch is created in the side of the tip section 14, resulting in an opening in the off-axis lumen 26 carrying the puller wire 32. The cross piece 47 lies transversely within the notch. Because the length of the ribbon forming the cross-piece 47 is longer than the diameter of the opening into the off-axis lumen 26, the anchor 44 cannot be pulled completely into the off-axis lumen 26. The notch is then sealed with polyurethane glue or the like to give a smooth outer surface. The glue flows into the off-axis lumen 26 to fully secure the anchor. A tunnel (not shown), in the form of polyimide tubing or the like, can be provided to permit passage of the lead wire 30 through the glue so that this same puller wire anchor construction can be used in the second off-axis lumen 28. Other means for anchoring the puller wires 32 in the tip section 14 would be recognized by those skilled in the art and are included within the scope of the invention.

In the depicted embodiment, the distal ends of the puller wires 32 are attached to opposite sides of the tip section 14. This design permits deflection of the tip section 14 in opposing directions. In another embodiment, the puller wires 32 can be attached at different locations along the length of the tip section 14, i.e., with the distal end of one puller wire anchored proximal the distal end of the other puller wire. Such a design would permit deflection at different points along the length of the tip section.

The catheter 10 further comprises two compression coils 46, each in surrounding relation to a corresponding puller wire 32, as shown in FIGS. 2 and 3. Each compression coil 46 is made of any suitable metal, such as stainless steel. Each compression coil 46 is tightly wound on itself to provide flexibility, i.e., bending, but to resist compression. The inner diameter of each compression coil 46 is slightly larger than the diameter of its associated puller wire 32. For example, when a puller wire 32 has a diameter of about 0.007 inch, the corresponding compression coil 46 preferably has an inner diameter of about 0.008 inch. The coating on the puller wires 32 allows them to slide freely within the compression coil 46. The outer surface of each compression coil 46 is covered along most of its length by a flexible, non-conductive sheath 48 to prevent contact between the compression coil 46 and the lead wires 30 within the central lumen 18. A non-conductive sheath 48 made of thin-walled polyimide tubing is presently preferred.

At the distal end of the catheter body, the two compression coils 46 are positioned in diametric opposition within the stiffening tube 22 and spacer 36 so that they can be aligned with the two off-axis lumens 26 and 28 in the tip section 14. The compression coils 46 and stiffening tube 22 are sized so that the compression coils 46 fit closely and slidably within the stiffening tube 22. With this design, the lead wires 30 distribute themselves around the two compression coils 46 without misaligning the coils.

The compression coils 46 are secured within the catheter body 12 with polyurethane glue or the like. Each compression coil 46 is anchored at its proximal end to the proximal end of the stiffening tube 22 in the catheter body 12 by a glue joint (not shown). When a stiffening tube 22 is not used, each compression coil is anchored directly to the outer wall 20 of the catheter body 12.

The distal end of each compression coil 46 is anchored to the distal end of the stiffening tube 22 in the catheter body 12 by a glue joint 52, or directly to the distal end of the outer wall 20 of the catheter body 12 when no stiffening tube 22 is used. Alternatively, the distal ends of the compression coils 46 may extend into the off-axis lumens 26 and 28 of the tip section 14 and are anchored at their distal ends to the proximal end of the tip section 14 by a glue joint. In the depicted embodiment, where the compression coils 46 are each surrounded by a sheath 48, care should be taken to insure that the sheath is reliably glued to the compression coil. The lead wires 30 can also be anchored in the glue joint. However, if desired, tunnels in the form of plastic tubing or the like can be provided around the lead wires at the glue joint to permit the lead wires to be slidable within the glue joint.

The glue joints preferably comprise polyurethane glue or the like. The glue may be applied by means of a syringe or the like through a hole made between the outer surface of the catheter body 20 and the central lumen 18. Such a hole may be formed, for example, by a needle or the like that punctures the outer wall 20 and the stiffening tube 22 that is heated sufficiently to form a permanent hole. The glue is then introduced through the hole to the outer surface of the compression coil 46 and wicks around the outer circumference to form a glue joint about the entire circumference of each sheath 48 surrounding each compression coil 46. Care must be taken to insure that glue does not wick over the end of the coil so that the puller wire cannot slide within the coil.

Within the off-axis lumens 26 and 28, each puller wire 32 is surrounded by a plastic sheath 42, preferably made of Teflon®. The plastic sheathes 42 prevent the puller wires 32 from cutting into the wall of the tip section 14 when the tip section is deflected. Each sheath 42 ends near the distal end of each puller wire 32. Alternatively, each puller wire 32 can be surrounded by a compression coil where the turns are expanded longitudinally, relative to the compression coils extending through the catheter body, such that the surrounding compression coil is both bendable and compressible.

Longitudinal movement of a puller wire 32 relative to the catheter body 12, which results in deflection of the tip section 14 in the direction of the side of the tip section to which that puller wire is anchored, is accomplished by suitable manipulation of the control handle 16. A suitable bidirectional control handle for use in the present invention is described in copending application Ser. No. 09/822,087, filed Mar. 30, 2001 and entitled "Steerable Catheter with a Control Handle Having a Pulley Mechanism", the disclosure of which is incorporated herein by reference. Other suitable bidirectional control handles are described in U.S. Pat. Nos. 6,123,699, 6,171,277, 6,183,463, and 6,198,974, the disclosures of which are incorporated herein by reference.

Alternatively, the catheter can be unidirectional, having only a single puller wire extending through an off-axis lumen. Examples of suitable unidirectional catheter designs and control handles for use in the present invention are disclosed, for example, in U.S. Pat. Nos. Re 34,502 and 5,897,529, the disclosures of which are incorporated herein by reference.

The tip section 14 includes a mechanism for enhancing control over the deflection of the tip section. The mechanism comprises one or more stabilizing features extending longitudinally along at least a portion of the length of the tip section 14. The stabilizing features are positioned generally symmetrically about a diameter D of the tip section, where that diameter corresponds to the plane in which the catheter is deflectable. In the case of a bidirectional catheter, that diameter D corresponds to the diameter along which both lumens 26 and 28 are positioned. In the case of a unidirectional catheter, the lumen in which the puller wire is anchored lies along the diameter D. The stabilizing features comprising a material that has a higher modulus of elasticity than the plastic that forms the tip section 14.

The stabilizing features should be generally rigidly in place relative to the tip section 14 so that the stabilizing features cannot shift, longitudinally, radially or circumferentially, relative to the tip section. Preferably the stabilizing features are fixedly attached to the tip section, e.g., by being coextruded with the tip section or by being glued with polyurethane glue or the like. Where the stabilizing features are not fixedly attached to the tip section, they should be confined to regions that are approximately the same size as the stabilizing features so that the stabilizing features do not shift within the regions.

In the embodiment of FIG. 5A, the tip section 14 includes two stabilizing features in the form of rods 54. The rods 54 are preferably made of metal, but could also be made of a suitable plastic. The rods 54 extend through the outer layer 27 on opposite sides of the tip section 14 so that they are both positioned along a diameter D. During manufacturing, the rods 54 are preferably coextruded with the outer layer 27, although the rods could instead be inserted in small lumens formed in the outer layer. Where the rods 54 are made of metal, preferably the rods are not exposed on the outside of the tip section. The two off-axis lumens 26 and 28 are positioned on opposing sides of the diameter D. Longitudinal movement of one of the puller wires 32 results in deflection of the tip section across the diameter D.

This arrangement improves the in-plane deflection of the tip section 14 because the less-elastic stabilizing features (e.g., the rods 54) reduce the tip section's tendency to bend in a direction other than across the diameter along which the stabilizing features are positioned. The stabilizing features also act to increase the lateral tip stability, which results in the user being able to create a greater contact force against the heart tissue. Thus, the catheter exhibits increased ablation stability.

FIG. 5B depicts an alternative embodiment in which the tip section 14 includes two stabilizing features in the form of strips 56, preferably made of plastic, positioned in the outer layer 27. The strips 56, like the rods 54 described above, are provided on opposite sides of the tip section 14 so that they are both positioned along a diameter D. Preferably the strips 56 are coextruded with the outer layer 27. The strips 56 function in a manner similar to the rods 54. The precise shape of the stabilizing features located in the outer layer 27 is not critical and can vary based on the application.

FIG. 5C depicts another alternative embodiment in which the tip section 14 includes two pie-shaped stabilizing features 58 in the core 24. Preferably the stabilizing features 58 are coextruded with the core 24.

It is generally preferred that the stabilizing features be located as far from the axis of the tip section 14 as possible. In the case where the stabilizing features are located within the core, for example, as shown in FIG. 5C, it is preferred that the bulk of the mass of each stabilizing feature be positioned away from the axis.

FIG. 5D depicts yet another alternative embodiment in which the tip section 14 includes a single bar-shaped stabilizing feature 60 positioned in the core 24 along the diameter D corresponding to the plane in which the catheter is deflectable. Preferably the stabilizing feature 60 is coextruded with the core 24. The single stabilizing feature can take any other suitable shape, such as an oval, that meets the criteria set forth above.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Accordingly, the foregoing description should not be read as pertaining only to the precise structures described and illustrated in the accompanying drawings, but rather should be read consistent with and as support to the following claims which are to have their fullest and fair scope.

What is claimed is:

1. A steerable catheter comprising:
   an elongated, flexible tubular catheter body having proximal and distal ends and a lumen extending therethrough;

a tip section at the distal end of the catheter body, the tip section comprising a flexible plastic tubing having a core and an outer layer surrounding the core, the core having at least one off-axis lumen extending therethrough;

a control handle at the proximal end of the catheter body;

a puller wire extending through the off-axis lumen of the tip section and lumen of the catheter body, and having a proximal end anchored to the control handle and a distal end anchored to the tip section, whereby the puller wire is longitudinally moveable relative to the catheter body to cause deflection of the tip section in a plane in a first direction; and one or more stabilizing features extending longitudinally along at least a portion of the length of the tip section and positioned in the outer layer of the tip section generally symmetrically about a diameter of the tip section corresponding to the plane in which the tip section is deflectable, the one or more stabilizing features comprising a material that has a higher modulus of elasticity than the plastic of the tip section.

2. A catheter according to claim 1, wherein the tip section is more flexible than the catheter body.

3. A catheter according to claim 1, wherein the one or more stabilizing features are generally rigid in place relative to the tip section.

4. A catheter according to claim 1, wherein two stabilizing features are provided in the outer layer on opposite sides of the core.

5. A catheter according to claim 4, wherein each stabilizing feature comprises a metal rod.

6. A catheter according to claim 5, wherein the metal rods are coextruded with the outer layer.

7. A catheter according to claim 4, wherein each stabilizing feature comprises a plastic strip.

8. A catheter according to claim 7, wherein the plastic strips are coextruded with the outer layer.

9. A catheter according to claim 4, wherein the tip section further comprises a braided mesh between the outer layer and the core.

10. A catheter according to claim 9, wherein the tip section further comprises an inner layer between the braided mesh and the core.

11. A catheter according to claim 1, wherein the tip section further comprises a braided mesh between the outer layer and the core.

12. A catheter according to claim 1, having a second off-axis lumen in the core of the tip section and further comprising a second puller wire extending through the second off-axis lumen, the second puller wire having a proximal end anchored to the control handle and a distal end anchored to the tip section, whereby the puller wire is longitudinally moveable relative to the catheter body to cause deflection of the tip section in the plane in a second direction opposite the first direction.

13. A catheter according to claim 12, wherein the tip section is more flexible than the catheter body.

14. A catheter according to claim 12, wherein the one or more stabilizing features are generally rigidly in place relative to the tip section.

15. A catheter according to claim 12, wherein two stabilizing features are provided in the outer layer on opposite sides of the core.

16. A catheter according to claim 15, wherein each stabilizing feature comprises a metal rod.

17. A catheter according to claim 16, wherein the metal rods are coextruded with the outer layer.

18. A catheter according to claim 15, wherein each stabilizing feature comprises a plastic strip.

19. A catheter according to claim 18, wherein the plastic strips are coextruded with the outer layer.

20. A catheter according to claim 15, wherein the tip section further comprises a braided mesh between the outer layer and the core.

21. A catheter according to claim 20, wherein the tip section further comprises an inner layer between the braided mesh and the core.

22. A catheter according to claim 12, wherein the tip section further comprises a braided mesh between the outer layer and the core.

23. A catheter according to claim 1, wherein the one or more stabilizing features each have a generally round cross-sectional area.

24. A catheter according to claim 1, wherein the core comprises a first material and the outer layer comprises a second material that is different from the first material.

25. A catheter according to claim 1, wherein the core comprises a substantially solid material.

26. A steerable catheter comprising:

an elongated, flexible tubular catheter body having proximal and distal ends and a lumen extending therethrough;

a tip section at the distal end of the catheter body, the tip section comprising a flexible plastic tubing comprising a core and an outer layer surrounding the core, the core having a longitudinal axis and at least one off-axis lumen extending therethrough;

a control handle at the proximal end of the catheter body;

a puller wire extending through the off-axis lumen of the core of the tip section and lumen of the catheter body, and having a proximal end anchored to the control handle and a distal end anchored to the tip section, whereby the puller wire is longitudinally moveable relative to the catheter body to cause deflection of the tip section in a plane in a first direction; and one or more stabilizing features extending longitudinally along at least a portion of the length of the tip section and positioned generally symmetrically about a diameter of the tip section corresponding to the plane in which the tip section is deflectable, the one or more stabilizing features also extending from or through the longitudinal axis and comprising a material that has a higher modulus of elasticity than the plastic of the tip section, wherein the one or more stabilizing features extend through the longitudinal axis of the core of the tip section.

27. A catheter according to claim 26, wherein two stabilizing features are provided in the core and each stabilizing feature extends from the longitudinal axis.

28. A catheter according to claim 26, wherein a single stabilizing feature is provided in the core and extends through the longitudinal axis.

29. A steerable catheter comprising:

an elongated, flexible tubular catheter body having proximal and distal ends and a lumen extending therethrough;

a tip section at the distal end of the catheter body, the tip section comprising a flexible plastic tubing having at least two off-axis lumens extending therethrough;

a control handle at the proximal end of the catheter body;

at least two puller wires extending through the lumen of the catheter body, whereby each puller wire has a proximal end anchored to the control handle and a distal end anchored to the tip section, is longitudinally moveable relative to the catheter body and extends through a different one of the off-axis lumens of the tip section to cause deflection of the tip section in a plane in a different direction; and one or more stabilizing features extending in a first dimension along at least a portion of the length of the tip section and having a portion extending in a second dimension between the two off axis lumens, the one or more stabilizing features comprising a material that has a higher modulus of elasticity than the plastic of the tip section.

30. A steerable catheter of claim 29, wherein the stabilizing feature has a generally rectangular cross-sectional area.

31. A catheter according to claim 30, wherein the stabilizing features are coextruded with the core.

32. A steerable catheter of claim 29, wherein each of the stabilizing features has a generally pie-shaped cross-sectional area.

33. A steerable catheter of claim 29, wherein the one or more stabilizing features extend across the tip section along a diameter in the second dimension thereof generally perpendicular to the plane of deflection of the tip section.

34. A steerable catheter of claim 29, wherein the tip section includes a core and an outer layer surrounding the core.

35. A steerable catheter of claim 34, wherein the lumens, the puller wires and the stabilizing features are positioned in the core.

* * * * *